United States Patent [19]

McArthur

[11] 4,064,152

[45] Dec. 20, 1977

[54] THERMALLY STABLE NICKEL-ALUMINA CATALYSTS USEFUL FOR METHANATION

[75] Inventor: Dennis P. McArthur, Yorba Linda, Calif.

[73] Assignee: Union Oil Company of California, Los Angeles, Calif.

[21] Appl. No.: 651,646

[22] Filed: Jan. 23, 1976

Related U.S. Application Data

[63] Continuation-in-part of Ser. No. 586,946, June 16, 1975, abandoned.

[51] Int. Cl.$^2$ ............................ C07C 1/04; C07C 1/12
[52] U.S. Cl. .......................... 260/449.6 M; 252/466 J; 48/214 A
[58] Field of Search .................... 260/449.6 M, 449 M

[56] References Cited

U.S. PATENT DOCUMENTS

| | | | |
|---|---|---|---|
| 3,156,657 | 11/1964 | Pinder et al. | 250/466 S |
| 3,361,535 | 1/1968 | Pollitzer et al. | 260/449 M X |
| 3,379,505 | 4/1968 | Holmes et al. | 260/449 M |
| 3,450,514 | 6/1969 | Sinfelt et al. | 260/449 M |
| 3,549,556 | 12/1970 | Dienes | 260/449 M X |
| 3,890,113 | 6/1975 | Child | 260/449 M X |

*Primary Examiner*—Howard T. Mars
*Attorney, Agent, or Firm*—Lannas S. Henderson; Richard C. Hartman; Dean Sandford

[57] ABSTRACT

Nickel-alumina catalysts having a remarkably high degree of thermal stability, and active for the hydrogenation of carbon oxides (methanation), are prepared by a novel "precipitative-occlusion" method. This method involves digesting a slurry of an alumina hydrate in an aqueous solution of an amino complex of a nickel salt. The digestion is carried out at a temperature sufficiently high to decompose the amino complex and "release" the nickel (II) ions. This results in a gradual precipitation of nickel hydroxide in the pores and interstices formed by the agglomerating particles of alumina hydrate. The coflocculated solids are recovered as by filtration, washed, dried and calcined. The resulting compositions are found, in high temperature reactions such as methanation, to retain their activity for much longer periods of time than do conventional nickel-alumina catalysts prepared by the most widely used prior art technique, viz., coprecipitation.

6 Claims, No Drawings

THERMALLY STABLE NICKEL-ALUMINA CATALYSTS USEFUL FOR METHANATION

RELATED APPLICATIONS

This application is a continuation-in-part of Ser. No. 586,946, filed June 16, 1975, now abandoned.

BACKGROUND AND SUMMARY OF INVENTION

In many nickel-catalyzed, high-temperature processes such as methanation, a long standing problem has been that of maintaining activity of the catalyst over extended periods of time. In such processes, deactivation can occur over process temperature ranges of about 500° – 2500° F as a result of sulfur poisoning, to which the nickel-alumina catalysts are extremely susceptible. At temperatures above about 1100° – 1200° F, deactivation can also occur as a result of nickel-crystallite growth, with resultant reduction in active surface area.

Nickel-alumina catalysts for use in the aforementioned processes must for maximum effectiveness contain relatively large proportions of nickel, generally in excess of about 20 wt. % and usually between about 30 and 60 percent by weight as NiO. This requirement places certain limitations on practical methods for manufacturing such catalysts. Conventional impregnation techniques of preformed alumina supports with nickel salt solutions require multiple impregnations with intervening calcinations, and generally result in catalysts having an unacceptably low pore volume. Comulling the powdered alumina base with sufficient concentrated nickel salt solution to provide an extrudable mixture generally does not give the desired nickel content and may also adversely affect porosity.

To avoid the foregoing difficulties, the art has been forced to resort to two principal catalyst manufacturing methods. One involves simply comulling the powdered alumina base with finely powdered nickel oxide, and then tableting or extruding the mixture. The resulting catalysts display poor activity and thermal stability due to poor nickel dispersion and minimal interaction with the alumina component. Somewhat more effective catalysts are prepared commercially by aqueous coprecipitation methods, in which aluminum hydroxide and nickel hydroxide are coprecipitated from an aqueous solution of salts of the two metals upon addition thereto of a base such as ammonium hydroxide. The most effective of such coprecipitated catalysts which I have found described in the literature is that of U.S. Pat. No. 3,320,182 to Taylor et al, which discloses a coprecipitated nickel-alumina catalyst, employing as the precipitant, ammonium bicarbonate. However, as will be shown hereinafter this catalyst, as well as other coprecipitated species, are very definitely inferior in thermal stability, compared to the catalysts of this invention.

In brief summary, the catalysts of this invention are prepared by precipitation of nickel hydroxide in a slurry consisting of a powdered alumina hydrate dispersed in an aqueous solution of an amino complex of a nickel salt. After thoroughly mixing the slurry at a temperature sufficiently low to avoid decomposition of the ammino complex, heat is applied to the mixture with vigorous agitation to effect a gradual decomposition of the ammino complex with resultant liberation of ammonia. This results in a very gradual precipitation of nickel hydroxide within the fine pore structure of the alumina hydrate particles and upon their external surfaces. The rate of precipitation is controlled by the heat input. Ordinarily, the slurry is brought to boiling to expel excess ammonia. When the precipitation is completed, the solids are collected as by filtration, washed, dried and subjected to a calcination which is believed to bring about formation of substantial quantities of nickel aluminate. The calcined powder can then be mulled and extruded, or tableted to form the desired catalyst shape. No added binder is ordinarily required. The tableted or extruded material is then again calcined in air at, e.g., 900° F.

A critical feature in the foregoing preparation is believed to reside in the use of an alumina hydrate, preferably boehmite, in the aqueous slurry from which nickel hydroxide is precipitated. The hydrated aluminas are believed to foster the combination therewith of nickel hydroxide, resulting ultimately in the formation of a substantial moiety of nickel aluminate. While the remarkable thermal stability of the present catalysts cannot be accounted for with certainty, it is believed that the active species of nickel in the finished catalyst is in a metallic form which can gradually become poisoned by sulfur or reduced in activity by crystallite growth. The nickel aluminate component is very difficultly reducible, and does not per se contribute any significant catalytic activity. However, it is believed that the nickel aluminate, or some such similar compounds, acts somewhat as a "reservoir" which, upon gradual reduction during use in the presence of hydrogen and/or carbon monoxide-containing gases, continually generates fresh metallic nickel, thus accounting for the remarkable activity maintenance of the catalysts.

DETAILED DESCRIPTION

The alumina hydrates employed as starting materials herein may comprise any one or more of the well known trihydrates such as bayerite or gibbsite, or the monohydrates, diaspore or boehmite, including gelatinous "pseudoboehmite". Spray-dried boehmite is the preferred material. Other forms of alumina are relatively non-reactive with nickel hydroxide and yield catalysts of inferior thermal stability. The pore volume of the hydrates utilized should range between about 0.1 and 3.0, preferably between 0.3 and 2.5 ml/g.

The ammino complexes utilized herein as a source of nickel hydroxide may comprise any of the well known water-soluble complexes of nickel salts containing at least 2 and preferably at least 4 ammino ligands per molecule. Many nickel salts are known to form such complexes, including the nitrate, chloride, bromide, formate, acetate, sulfate, etc. In general however, only the complexes containing either 4 or 6 ammino ligands per molecule are known to exist as stable solids, but their preparation in pure form is rather cumbersome, and it is therefore preferred to form the complex or complexes integrally with the manufacture of the catalyst. In essence, this is accomplished by adding suitable quantities of ammonia to an aqueous solution of the desired nickel salt. This conventional technique does however present some difficulties. Upon the initial addition of ammonia, nickel hydroxide precipitates, and does not readily redissolve in the form of ammino complexes unless one resorts to the use of large excesses of ammonia and/or extended digestion periods. I have found however that these difficulties can be very conveniently avoided by using a novel "buffering" technique, which permits substantially instantaneous formation of dissolved ammino complexes, while using only the required stoichiometric quantities of ammonia.

According to this preferred technique, a minor proportion of an ammonium salt, preferably of the same anion as that of the nickel salt utilized, is dissolved in the nickel salt solution, either prior to or simultaneously with, the addition of ammonia. The ammonium salt may either be added as such, or an acid of the desired anion may be added to the nickel salt solution, and subsequently neutralized with the initial increments of ammonia added to the solution. Effective amounts of ammonium salt may range between about 0.1 and 1.0 mole, preferably about 0.2 – 0.7 mole, per mole of nickel salt in solution. The mechanism by which the ammonium salt "buffers" (a term which may be a misnomer) the solution to obtain the desired result is believed to involve a mass action phenomenon resulting from an increase in ammonia concentration and/or a decrease in hydroxyl ion concentration, whereby inhibiting the $Ni(OH)_2$-forming reaction. The observed effect is that upon addition of ammonia no precipitation of nickel hydroxide occurs, and the rapid change in color of the solution indicates a substantially instantaneous formation of the desired ammino complex in solution. No excess of ammonia is required over the amount required to provide the desired stoichiometric ratio of ammino ligands per mole of nickel salt.

Using nickel nitrate hexahydrate as an exemplary salt, it has been speculated in the literature (Handbook of Chemistry and Physics, 48th ed., The Chemical Rubber Co., Clev., Ohio (1967-1968).) that when ammonia is added to a solution of nickel nitrate, all of the following ammino complexes may exist in transient or equilibrium states in solution:

$$Ni(NH_3)(H_2O)_5(NO_3)_2 \quad (1)$$

$$Ni(NH_3)_2(H_2O)_4(NO_3)_2 \quad (2)$$

$$Ni(NH_3)_3(H_2O)_3(NO_3)_2 \quad (3)$$

$$Ni(NH_3)_4(H_2O)_2(NO_3)_2 \quad (4)$$

$$Ni(NH_3)_5(H_2O)(NO_3)_2 \quad (5)$$

$$Ni(NH_3)_6(NO_3)_2 \quad (6)$$

As noted above, only complexes (4) and (6) are known to exist in stable form. It would thus appear at first hand that it would be necessary to utilize 4 moles, and up to about 6 moles, of ammonia per mole of nickel salt to achieve a stable solution. However, such is not necessarily the case. Even if only sufficient ammonia is added to yield complexes (1), (2) or (3), and assuming that the existence of such complexes is only transient, the added ammonia would ultimately form the stable complexes (4) and/or (6), leaving a substantial portion of the dissolved nickel salt in uncomplexed form. Such partially complexed solutions can be operatively utilized for purposes of the present invention. The invention basically requires only that (I) all of the nickel be in solution prior to the addition of the alumina hydrate, and (2) that sufficient ammonia be complexed with the dissolved nickel salt to provide, on subsequent decomposition of the complex, sufficient ammonium hydroxide to precipitate essentially all of the nickel as nickel hydroxide, as e.g.:

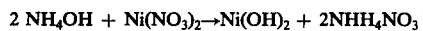

$$2\,NH_4OH + Ni(NO_3)_2 \rightarrow Ni(OH)_2 + 2NHH_4NO_3$$

The foregoing explains why the minimum theoretical mole-ratio of ammino ligands per mole of nickel salt to obtain ultimately complete precipitation of nickel hydroxide is only 2. However, it must be realized that when minimum ratios of ammonia are utilized certain precautions must be observed. During the subsequent decomposition at elevated temperatures in an open vessel at atmospheric pressure, some of the liberated ammonia will escape from the solution in gaseous form. Excessive loss of ammonia could preclude complete precipitation of the nickel. Ammonia loss could be prevented with the use of a pressure vessel, but this approach would require extended periods of time. Hence, in order to ensure complete precipitation and to avoid the necessity for a pressure vessel, it is preferred to provide between about 4 and 6 moles of ammonia per mole of nickel salt. Amounts in excess of 6 moles may be utilized, but are unnecessary and merely extend the time required to expel excess ammonia from the solution.

It will be understood that the above described ammination of the nickel salt solution should be carried out at relatively low temperatures so as to avoid premature decomposition of the ammino complex. In general, temperatures below about 60° and preferably below about 50° C should be maintained prior to addition of the alumina hydrate component. It should be understood also that the initial nickel salt solution should be sufficiently dilute that upon subsequent addition of the alumina hydrate component, an easily stirrable slurry will be obtained. To this end, nickel salt concentrations ranging between about 0.2 and 5 M, preferably between 0.4 and 0.9 M, are generally utilized to provide composites containing between about 5 and 70, preferably between 40 and 65 weight-percent NiO, the balance being alumina.

To the amminated solution prepared as described above is then added, preferably in small increments with constant, vigorous stirring, the desired proportion of the alumina component. Sufficient holding time should be allowed for the solution to fill the pores of the alumina particles, generally between about 2 minutes and 30 minutes. After time has been allowed for pore saturation the slurry is heated with continued agitation to decomposition temperatures, generally between about 80° and 110°, and preferably about 90° – 100° C. The slurry is then digested at such temperatures for about 0.1–6 hours, normally about 1–5 hours, while maintaining continuous agitation.

During the digestion period, some ammonia is liberated from the solution, the nickel ammino complexes are decomposed, and nickel hydroxide is formed. The nickel hydroxide is believed to form within the pores and on the surfaces of the alumina particles. In addition, it is believed that a nickel hydroxide phase is occluded in the interstices formed by the agglomerating alumina particles.

The rate of precipitation of $Ni(OH)_2$ during the digestion period has an important bearing on the nature of the product obtained. It has been found that if the precipitation is too rapid, a more or less non-homogeneous product is obtained in which some of the nickel appears in the form of large agglomerates, distinct from a phase in which the nickel is more intimately composited with the $Al_2O_3$. This phenomenon is especially apt to occur in nickel-rich composites, containing more than about 30 weight-percent of NiO. It is therefore preferred to precipitate no more than about 1.5 moles of $Ni(OH)_2$ per mole of alumina per hour. This is accomplished primarily by controlling the heat input to the slurry, and can be monitored by detecting a gradual decline in pH of the slurry, from an initial value of about 8-12, to a final value of about 6-7.

At the conclusion of the digestion period the slurry is normally greyish-greenish-blue in color. Completion of the desired precipitation can be easily detected by allowing a small portion of the slurry to settle, and adding ammonia to the supernatant solution. The absence of blue coloration indicates essentially complete precipitation of nickel.

Upon completion of the nickel hydroxide precipitation, the slurry is filtered and the filter cake washed in conventional manner to remove soluble salts therefrom. Both the filtrate and the wash solutions are water clear and virtually completely free of nickel. The filter cake is then dried in conventional manner and calcined at temperatures of about 400° - 1000° F. The calcined powder can then be shaped into tablets or extrudates of the desired size (e.g., 1/32 - ¼ inch), generally without the need for an added binder. However, in some cases it may be desirable to utilize about 10-20 weight-percent of a peptized alumina binder. The shapes catalyst is then given a final calcination in air at temperatures of between 750° and 1000° F for 1 - 2 hours.

X-ray diffraction analysis of the catalysts prepared as described above indicates the presence of gamma alumina, crystallite size 20-60 angstroms, and nickel oxide crystallites in the size range of about <20-300 angstroms, depending on the nickel content. In view of their high thermal stability and activity, the presence of large nickel oxide crystallites is rather surprising.

USE OF CATALYSTS

Catalysts prepared as described above are highly useful in the hydrogenation of carbon oxides (methanation) to produce methane, a reaction which is generally carried out at temperatures ranging between about 600° and 1500° F and pressures between about 100-1500 psig. This process is used primarily for the production of substitute natural gas (SNG) from gas mixtures rich in $CO$ and/or $CO_2$ and for the purification of synthesis gases rich in hydrogen, but still containing minor amounts of carbon monoxide (which poisons ammonia synthesis catalysts). The methanation reaction is extremely exothermic, and much difficulty has been encountered in controlling temperature rise in the reactor. One widely used technique under adibatic conditions involves the recycle of large volumes of product gas (mainly methane) to serve as a heat sink, thus adding greatly to operating costs.

Catalysts previously available for this process have been found to become rapidly deactivated if temperatures in excess of about 1100° - 1200° F are reached. Some activity at temperatures above 1200° is usually retained, but at these high temperatures the equilibrium for methanation is unfavorable; it is therefrom a practical necessity to carry out a terminal portion of the methanation at temperatures below 1100° F in order to achieve high conversions. An ideal catalyst for methanation should hence retain its activity at both the high and low methanation temperatures. Retention of activity at high temperatures raises permissible exothermic temperature rises thereby reducing or eliminating the need for expensive temperature control measures. The catalysts of this invention appear to meet all methanation process requirements to a much greater extent than those which are now commercially available or described in the literature.

The following examples are cited to illustrate the invention, but are not to be construed a limiting in scope:

EXAMPLE 1 -(CATALYST AA-8872)

To 2000 ml of an aqueous nickel nitrate solution containing 263 grams of nickel nitrate hexahydrate was added 40 ml of concentrated nitric acid. Then, concentrated ammonium hydroxide (340 ml) was added slowly to the nickel nitrate solution to form initially ammonium nitrate with the nitric acid, and then an ammino complex with the nickel nitrate. Vigorous stirring was maintained during the solution preparation stage. Then 76 grams of spray-dried boehmite alumina powder (pore volume ~3 ml/g) were added. A period of 5 minutes was allowed for the complexed salt solution to completely fill the pores of the alumina particles. The resultant slurry was heated from ~30° C to 96° C over a period of one hour, and then digested at a temperature of about 97° C for about 2 hours while maintaining vigorous stirring throughout the digestion period. The initial pH of the slurry was about 8.9. At the end of the digestion period the slurry had become blue-green in color, and was filtered on a Buchner funnel. No color change was observed upon addition of concentrated ammonium hydoxide to the filtrate, indicating that the nickel had been substantially completely precipitated. The pH of the filtrate was about 6.3. The filter cake was then washed with 1500 ml of hot water and oven-dried overnight at 110° C. Two such batches of oven-dried filter cake were prepared and combined to yield 336 grams. This material was then calcined in air at 750° F for two hours to decompose any remaining nitrates. The resulting powder was dark grey-green in color.

The calcined powder was placed in a muller and dryground for about one hour, and then 215 ml of distilled water were added, and the mixture was mulled for 10 minutes. At this point the mull appeared to be too wet and was hence partially dried with a hot air gun for 30 minutes. Mulling was then continued for an additional 30 minutes. At this point, 2.5 grams of methyl cellulose and 10 ml of water were added, and the mulling continued for 10 minutes more.

The finished mull was extruded through a 1/16-inch diameter die at 2000 psig, and the resulting extrudate was dried in a forced air oven at 110° C, and then calcined in air at 900° F for two hours. The resulting product contained 53.6 weight-percent NiO, had a surface area of 182 m²/g, a pore volume of 0.52 cc/g, and showed by X-ray analysis the presence of gamma alumina and a nickel oxide phase in the form of crystallites of average diameter 200 angstroms. The predominant portion of the pore volume was in pores of 90-100 angstroms diameter.

EXAMPLE 2

This example details the preparation of a comparison catalyst prepared by coprecipitation according to the methods described in U.S. Pat. No. 3,320,182.

About 350 grams of $Ni(NO_3)_2.6H_2O$ and 450 grams of $Al(NO_3)_3.9H_2O$ were dissolved in 1800 ml $H_2O$. The solution was heated to 95° C and then, little by little, 413 grams of powdered $NH_4HCO_3$ was added, while maintaining the temperature at 95° C. Approximately 105 minutes were required to add the precipitant slowly enough to avoid loss by foaming. Periodic additions of hot water were made to make up evaporation losses.

A second preparation was made exactly as the above, except the addition time of $NH_3HCO_3$ was 80 minutes (pushing the reaction to just short of overflow by foaming), and 425 grams thereof were added. The final pH in the two cases was 6.1 and 5.9, respectively, making an average of 6.0. The two batches were combined after filtration, dried at 250° F overnight and washed to remove excess nitrate. The washed product was then dried again at 250° F, mulled to an extrudable paste with water, and extruded through a 1/16 inch die. The extrudate was then dried at 250° F and calcined at 900° F for three hours. The final catalyst had a NiO content of 60.2% by weight (47.3% Ni) and a surface area of 200 $m^2/g$.

EXAMPLE 3 - ACTIVITY TESTING

The foregoing catalysts, along with two commercial methanation catalysts, were tested for thermal stability in a special high temperature methanation test. The commercial catalysts were well known nickel-alumina compositions widely used in industry for purification of synthesis gas. The conditions of the test runs were as follows:

| Feed Gas Composition: | |
|---|---|
| $H_2$ | 30.9 vol. % |
| $CH_4$ | 9.6 |
| CO | 7.9 |
| $CO_2$ | 7.9 |
| $H_2O$ | 43.7 |
| Reactor Inlet Temperature | 900° F |
| Outlet Temperature | 1220° F (Calculated Adiabatic) |
| Pressure | 300 psig |
| Catalyst Volume | 85 ml (13" bed length) |
| GHSV | 10,000 |

Since the reactor was heated in a fluidized sand bath, reaction conditions were not adiabatic. Typically, the peak temperatures were 1150° – 1175° F, dropping to about 925° F at the outlet as a result of cooling by the sand bath. The equilibrium composition established at the lower temperature corresponds to approximately 95% conversion of CO.

Thermocouples were placed at less than one-inch intervals in the catalyst bed and the temperature profile recorded as a function of time. As the catalysts deactivate, the peak temperature travels slowly down the bed and is picked up by successive thermocouples. The rate of deactivation is simply the number of days required for the peak to travel one inch. The greater the number of days required, the greater is the thermal stability of the catalyst. The results of the tests were as follows:

Table 1

| Catalyst | Method of Preparation | Wt. % NiO | Deactivation Rate, Days/Inch |
|---|---|---|---|
| Example I | Precipitative Occlusion | 53.6 | 183 |
| Example II | Coprecipitation | 60.2 | 113 |
| Commercial A | Coprecipitation | ~50* | 6.2 |
| Commercial B | Comulling | 37.6 | 0.9 |

*Estimated Value

It is apparent that the catalyst of Example I is very definitely superior to the three prior art catalysts.

EXAMPLE 4 - (CATALYST AA-8874)

This example illustrates a somewhat more expeditious method for preparing a catalyst very similar to that of Example I, using a reduced volume of slurry.

To one liter of an aqueous nickel nitrate solution containing 263 grams of nickel nitrate hexahydrate was added 80 ml of concentrated nitric acid. The solution was well mixed, and 340 ml of concentrated ammonium hydroxide solution were then added slowly as previously described. The solution temperature at this point had risen to about 65° C. After cooling the solution at about 37° C, 76 grams of the boehmite alumina described in Example 1 were stirred into the solution. After a five-minute period to allow for pore saturation of the alumina, the slurry was heated to 97° C over a period of ~1 hour, and then digested with stirring at that temperature for 1.75 hours.

The slurry was then filtered on a Buchner funnel and the filter cake washed with 1500 ml of hot water and dried overnight at 110° C. A second batch of filter cake was prepared in a similar manner, except that 375 ml of concentrated ammonium hydroxide was used, and the digestion time was ~3 hours. These two batches of dried filter cake were combined to yield 337 grams. This material was then calcined in air to 400° F for one hour and at 750° F for two hours in order to decompose any remaining nitrates.

The calcined powder was placed in a muller and mulled together with 2.5 grams of methyl cellulose and 160 ml of water. The mull was then extruded through a 1/16-inch diameter die at 1800 psig and the extrudates were air-dried overnight, oven dried at 110° C, air calcined at 400° F for one hour, and finally at 900° F for 2 hours. The resulting product contained 56.1 weight-percent NiO, had a surface area of 193 $m^2/g$, a pore volume of 0.54 cc/g, and showed by X-ray analysis the presence of gamma alumina and a nickel oxide phase in the form of crystallites of average diameter 175 angstroms. After reduction with hydrogen, the nickel surface area was found to be 7.0 square meters per gram of catalyst, as determined by hydrogen chemisorption. The pore size distribution was very similar to that of the catalyst of Example 1.

The following claims and their obvious equivalents are intended to define the true scope of the invention:

I claim:

1. In a process for the hydrogenation of carbon monoxide and/or carbon dioxide to form methane wherein a feed gas comprising hydrogen and carbon monoxide and/or carbon dioxide is contacted at a temperature between about 600° and 1500° F with a nickel catalyst to effect said hydrogenation, the improvement which comprises using as said catalyst an intimate composite of between about 30 and 95 percent alumina and about 5 and 70 percent nickel oxide by weight, said catalyst having been prepared by the steps of:

1. slurrying a powdered alumina hydrate in an aqueous solution of a nickel salt for a sufficient time to effect pore-saturation of said alumina hydrate with said solution, sufficient of said nickel salt being in the form of an ammino complex to provide at least 2 moles of ammino ligands per mole of said nickel salt;

2. heating the resulting slurry with agitation at a temperature and for a time sufficient to bring about a gradual decomposition of substantially all of said ammino complex with resultant liberation of ammonia and precipitation of substantially all of said nickel salt in the form of nickel hydroxide intimately composited with said powdered alumina hydrate; and 3. calcining the resulting composite at a temperature sufficiently high to convert said alumina hydrate to gamma alumina.

2. A process as defined in claim 1 wherein at least a portion of said contacting is carried out at above about 1100° F.

3. A process as defined in claim 1 wherein said nickel oxide is in the form of crystallites having an average diameter between about <20 and 300 A.

4. A process as defined in claim 1 wherein said alumina hydrate is boehmite.

5. A process as defined in claim 1 wherein said catalyst is in the form of aggregates having an average diameter between about 1/32 and ¼ inch.

6. A process as defined in claim 1 wherein said catalyst contains about 35 – 60% $Al_2O_3$ and about 40 – 65% NiO.

* * * * *